(12) United States Patent
Schüler

(10) Patent No.: US 11,260,521 B2
(45) Date of Patent: Mar. 1, 2022

(54) HAND GRIP ELEMENT WITH A HAND GRIP BODY FOR ACTIVATING AN UPRIGHT POSTURE OF THE HUMAN BODY

(71) Applicant: Horst Schüler, Münster (DE)

(72) Inventor: Horst Schüler, Münster (DE)

( * ) Notice: Subject to any disclaimer, the term of this patent is extended or adjusted under 35 U.S.C. 154(b) by 0 days.

(21) Appl. No.: 16/622,723

(22) PCT Filed: Jun. 4, 2018

(86) PCT No.: PCT/EP2018/064637
§ 371 (c)(1),
(2) Date: Dec. 13, 2019

(87) PCT Pub. No.: WO2018/228845
PCT Pub. Date: Dec. 20, 2018

(65) Prior Publication Data
US 2020/0101588 A1 Apr. 2, 2020

(30) Foreign Application Priority Data
Jun. 13, 2017 (DE) ...................... 10 2017 112 923.5

(51) Int. Cl.
*B25G 1/10* (2006.01)
*A61F 5/10* (2006.01)
(Continued)

(52) U.S. Cl.
CPC ................ *B25G 1/102* (2013.01); *A61F 5/10* (2013.01); *A61H 39/007* (2013.01); *A61H 39/04* (2013.01); *A63C 11/222* (2013.01)

(58) Field of Classification Search
CPC ....... F25G 1/102; A61H 39/007; A61H 39/04; A61F 5/10; G06F 3/03543; G06F 3/16
See application file for complete search history.

(56) References Cited

U.S. PATENT DOCUMENTS 2,237,381 A * 4/1941 Wallace ................. D06F 75/14
  38/77.7
4,592,109 A * 6/1986 Borea ................. A46B 5/0095
  15/144.1
(Continued)

FOREIGN PATENT DOCUMENTS

| DE | 29900206 U1 | 1/2000 |
| DE | 102004052681 A1 | 9/2005 |

(Continued)

OTHER PUBLICATIONS

International Search Report for Application No. PCT/EP2018/064637, with English translation, dated Sep. 19, 2018 (6 pages).

(Continued)

*Primary Examiner* — Victor D Batson
*Assistant Examiner* — Matthew J Sullivan
(74) *Attorney, Agent, or Firm* — Nixon Peabody LLP

(57) ABSTRACT

A grip element having an elongate grip body with a first end region and a second end region. The grip body has a first surface near the second end region, with a curved subregion for supporting a subregion of the ball of the human hand, and an outwardly curved second surface supporting a subregion of the palm, and an inwardly curved third surface adjacent to the first surface and supporting the extended thumb, and an outwardly curved fourth surface lying substantially opposite the third surface and supporting the middle finger, adjacent to which fourth surface an outwardly curved fifth surface is provided for supporting the ring finger. The grip body has a sixth surface to support the index finger. The sixth surface, starting from a subregion of the second surface spaced apart from the second end region of the grip body, extends in the direction to the first end region and runs longitudinally along the grip body.

18 Claims, 16 Drawing Sheets

(51) Int. Cl.
*A61H 39/00* (2006.01)
*A61H 39/04* (2006.01)
*A63C 11/22* (2006.01)

(56) References Cited

U.S. PATENT DOCUMENTS

| | | | |
|---|---|---|---|
| 5,556,902 A | 9/1996 | Theken | |
| 5,692,265 A | 12/1997 | Dalury | |
| 6,029,389 A * | 2/2000 | Newton | A01K 87/08 |
| | | | 43/21.2 |
| 6,106,418 A | 8/2000 | Hagey | |
| 6,823,562 B1 * | 11/2004 | Smith | B25G 1/06 |
| | | | 16/421 |
| 7,234,205 B2 * | 6/2007 | Blauer | A45B 9/02 |
| | | | 135/25.4 |
| 7,930,804 B2 * | 4/2011 | Cornfield | B25G 1/102 |
| | | | 16/430 |
| 8,092,411 B2 | 1/2012 | Betcher | |
| 8,152,396 B2 * | 4/2012 | Kuykendall | B43K 23/008 |
| | | | 401/6 |
| 8,438,769 B1 * | 5/2013 | Ghannam | F41C 23/16 |
| | | | 42/71.01 |
| 8,529,150 B2 * | 9/2013 | Olson | A46B 5/026 |
| | | | 401/286 |
| 8,833,620 B2 * | 9/2014 | Interdonato | A45F 5/00 |
| | | | 224/217 |
| 9,120,528 B2 * | 9/2015 | Badollet | B62K 21/26 |
| 10,300,592 B2 * | 5/2019 | Hayes | A46B 17/02 |
| 10,766,131 B2 * | 9/2020 | Deiser | B25G 1/102 |
| 2005/0137064 A1 | 6/2005 | Nothnagle | |
| 2009/0165233 A1 * | 7/2009 | Hagemann | A46B 5/02 |
| | | | 15/143.1 |
| 2010/0218347 A1 | 9/2010 | Lenhart | |
| 2018/0169852 A1 * | 6/2018 | Fryer-Biggs | B25G 1/102 |
| 2019/0216186 A1 * | 7/2019 | Shintani | B25G 1/102 |

FOREIGN PATENT DOCUMENTS

| | | |
|---|---|---|
| DE | 102004062905 A1 | 7/2006 |
| DE | 202010008487 U1 | 11/2010 |
| EP | 2168641 A1 | 3/2010 |
| WO | WO 2010/015000 A1 | 2/2010 |
| WO | WO 2012/176053 A1 | 12/2012 |

OTHER PUBLICATIONS

Written Opinion of International Searching Authority for Application No. PCT/EP2018/064637, with English translation, dated Sep. 19, 2018 (10 pages).

* cited by examiner

HAND GRIP ELEMENT WITH A HAND GRIP BODY FOR ACTIVATING AN UPRIGHT POSTURE OF THE HUMAN BODY

CROSS-REFERENCE TO RELATED APPLICATIONS

This application is a U.S. National Stage of International Application No. PCT/EP2018/064637, filed Jun. 4, 2018, which claims the benefit of Germany Patent Application No. 10 2017 112 923.5, filed Jun. 13, 2017, both of which are incorporated herein by reference in their entireties.

The present invention relates to a hand grip element with an elongated hand grip body with a first end region and, arranged at a distance thereto in the longitudinal direction of the hand grip body, a second end region according to the preamble of claim 1.

In various technical fields which also include the very general field of medical technology, quite different hand grip elements have already been made known.

Accordingly for example, DE 10 2004 062 905 A1 describes a device for stimulating acupressure points and lines, or respectively areas, and is therefore ascribable to a very distant field of medical technology.

DE 10 2004 052 681 A1 describes an ergonomically-shaped universal hand grip which is provided with an acupressure means and can be arranged on utensils from daily life such as a knife, and which is also intended to fulfill a medical function. The medical effect in this case is to be achieved in that the hand grip stimulates an acupressure point on the inside of the hand.

In DE 20 2010 008 487 U1, a therapeutic appliance was disclosed with a grip region to be enclosed by the hand and a seat surface for the thumb of the hand which is provided to be used by a therapist when treating a patient during massage in order to exert pressure on a place on the body of the patient to be treated.

DE 299 00 206 U1 describes an ergonomic hand grip that is to be used with sports equipment or tool handles as well, and that is to promote the use of the triceps and deltoid muscles. To this end, the hand grip known therefrom has a contour designed to be gripped with the hand, and also possesses a thumb rest.

U.S. Pat. No. 5,692,265 B1 describes an ergonomic hand grip which is provided to be, for example, integrated in a tool handle, and to this end has a hand grip which possesses ergonomically contoured contact surfaces for the fingers of the human hand.

Finally, U.S. Pat. No. 8,092,411 B1 describes a hand orthotic which is to hold the fingers of a patient separate from the palm during rehabilitation measures, or also during operations. To this end, the employed hand grip possesses contoured surfaces for accommodating the fingers, and a support surface for the thumb, and also a fixture in the form of an elastic enclosure with open ends in order to hold both the thumb as well as the fingers of the patient in place in the corresponding contoured surfaces of the hand grip. This known hand orthotic is therefore to counteract a tendency of the human hand to cramp in a position fixed over a long time in order to prevent the fingers from moving toward the palm and the fingernails from digging into the skin of the palm, and thus cause injuries to the palm.

This known hand grip element has an elongated hand grip body with a first end region and, arranged at a distance therefrom in the longitudinal direction of the hand grip body, a second end region, wherein the hand grip body has a first shaped surface adjacent to the second end region, with a curved subregion for supporting a subregion of the ball of the human hand, and an outwardly curved second shaped surface adjacent to the first shaped surface to support a subregion of the palm, and an inwardly curved third shaped surface adjacent to the first shaped surface to support the substantially extended thumb, and an outwardly curved fourth shaped surface that lies substantially opposite the third shaped surface to support the middle finger, and adjacent to which fourth shaped surface an outwardly curved fifth shaped surface is provided for supporting the ring finger, and the hand grip body has a sixth shaped surface provided to support the index finger.

The known hand grip element therefore already has a plurality of shaped surfaces that serve to accommodate or respectively support subregions of the human hand, or individual fingers as well. In accordance with the function of the known hand grip element, that is, to serve as a medical aid and to prevent the human hand from cramping and consequently, to prevent fingernails of individual fingers from penetrating into the palm, the known hand grip element also possesses a shaped surface for accommodating the index finger of the hand in a hand position that corresponds to an enclosing grasp of the known hand grip element.

The user of the known hand grip element should in fact be able to securely hold the hand grip element for a plurality of hours even under conditions of anesthesia in an enclosing, gripped position and therefore in a hand grip position that, on the one hand, keeps the fingers apart from each other and, on the other hand, also separates the fingernails of the index finger, the middle finger, the ring finger and the little finger from the palm.

In contrast thereto, the object of the present invention is to create a hand grip element that causes an independently occurring, natural and physiological alignment of the hands and forearms in the user or wearer, and can be used in different types of sports, and in particular during the natural standing, walking and running of the user. The hand grip element to be created should produce an upright and relaxed body posture of the user, and contribute to an improvement of the overall vitality and performance of the user due to positive sensorimotor effects, especially on the sympathetic part of the vegetative nervous system.

To achieve this objective, the invention has the features indicated in claim 1. Advantageous embodiments thereof are specified in the other claims.

The invention creates a hand grip element having an elongated hand grip body with a first end region and, arranged at a distance from the latter in the longitudinal direction of the hand grip body, a second end region, wherein the hand grip body has a first shaped surface located adjacent to the second end region, with a curved subregion for supporting a subregion of the ball of the human hand, and an outwardly curved second shaped surface located adjacent to the first shaped surface for supporting a subregion of the palm, and an inwardly curved third shaped surface located adjacent to the first shaped surface for supporting the substantially extended thumb, and an outwardly curved fourth shaped surface lying substantially opposite the third shaped surface for supporting the middle finger, adjacent to which fourth shaped surface an outwardly curved fifth shaped surface is provided for supporting the ring finger, and the hand grip body has a sixth shaped surface provided to support the index finger, wherein the sixth shaped surface, starting from a subregion of the second shaped surface spaced apart from the second end region of the hand grip body, extends toward the first end region and runs substantially in the longitudinal direction of the hand grip body.

The hand grip element according to the invention therefore possesses an elongated hand grip body with two end regions that oppose each other, between which the hand grip body has a plurality of shaped surfaces.

From the perspective of the wearer or user using the hand grip element who uses the hand grip element in a proper manner, the hand grip body possesses a first or front end region that, in the direction of the index finger adjacent to the hand grip body, is oriented toward the index finger, that is, faces away from the body of the wearer or user, whereas the second or rear end region points toward the body of the wearer or user when the hand grip element is properly used.

The first shaped surface is designed adjacent to the rear or second end region on the hand grip body and has a subregion that is designed to support a subregion of the ball of the hand, or respectively the thenar eminence of the human hand of the wearer or user of the hand grip element according to the invention.

Proceeding from an interior of the hand grip body, the subregion of the first shaped surface designed to support the thenar eminence is designed to curve inwardly so that the curved subregion of the thenar eminence directed outward when the human hand is extended can fit the inwardly curved subregion of the first shaped surface, and a touch-sensitive contact region between the thenar eminence and the subregion of the first shaped surface is therefore formed.

The hand grip body has an outwardly directed curved second shaped surface to support a subregion of the palm of the human hand, wherein when the hand grip element according to the invention is properly used, an inwardly curved subregion of the palm of the human hand comes to rest on the second shaped surface.

Moreover, the hand grip body has a third shaped surface that is adjacent to the first shaped surface and is inwardly curved and which is designed to support the substantially extended thumb. When the hand grip element according to the invention is properly used, the thumb of the hand lies against the inwardly curved third shaped surface by its outwardly directed curved thumb inner side, and assumes a substantially extended position so that the thumb tip of the thumb points forward and upward viewed by the user or wearer of the hand grip element according to the invention.

Moreover, the hand grip body has a curved fourth shaped surface which substantially lies opposite the third shaped surface and is directed outwardly which serves to support the middle finger of the hand of the wearer or user of the hand grip element according to the invention. In this case, the fourth shaped surface can be designed in the shape of a recess or trough in which the middle finger comes to lie with a proper hand posture of the wearer or user when using the hand grip element and fits against the shape of the recess or trough when the hand position of the wearer or user at least partially grasps the hand grip body.

The hand grip body moreover has a curved fifth shaped surface that is adjacent to the fourth shaped surface, extends toward the second or rear end region, is directed outward, and is provided to support the ring finger of the wearer or user of the hand grip element according to the invention, and against which the ring finger fits when the hand position of the user or wearer of the hand grip element grasps the hand grip body.

The hand grip element according to the invention moreover has, on the hand grip body, a sixth shaped surface which is also provided to support the index finger and, when viewed from the second, i.e., rear end region of the hand grip body, extends outward from a subregion of the second shaped surface at a distance from the second end region toward the first end region and substantially runs in the longitudinal direction of the hand grip body. The index finger of the wearer or user of the hand grip element according to the invention experiences a substantially straight-line and forwardly-directed position due to the sixth shaped surface so that the index finger assumes a position that is directed to the front away from the body of the wearer, i.e., in the direction of walking or running, or in the direction of sight when the user is standing, given a natural body posture of the wearer or user of the hand grip element when walking, standing or running.

The hand grip element according to the invention enables an independently occurring, natural and physiological orientation of the hands and forearms of the user or wearer to be supported, wherein this includes usage in different types of sports and in particular when the user naturally stands, walks and runs. The hand grip element also effectuates supporting and promoting an upright and relaxed body posture of the user, and contributes to an improvement of the overall vitality and bodily performance of the user due to positive effects on the sympathetic part of the vegetative nervous system.

It was surprisingly revealed that an effect is produced by the hand grip element according to the invention when used by a user or wearer that stabilizes the natural movement and natural, i.e., erect body posture, which is caused by the contact between the thenar eminence and the first shaped surface of the hand grip body, as well as the stabilizing orientation of the thumb and the index finger on the third shaped surface and the sixth shaped surface.

The contact of the first shaped surface with the thenar eminence and the subsequent region of the wrist oriented toward the wrist of the wearer or user causes a sensorimotor body reaction and a reflexive stimulation of the radial artery lying directly below the skin's surface, and accordingly instigates a contact stimulus of the circulatory system of the user or wearer and therefore an activation of the circulatory system. The alignment of the thumb and the index finger of the user or wearer by the configuration of the hand grip element according to the invention achieved by the third and by the sixth shaped surface leads to a body posture that straightens and stabilizes the body of the user or wearer.

This effect that stabilizes the upright body posture is advantageous for users or wearers of any age and has in particular a positive effect in such people who tend toward a less pronounced upright posture of the upper body, wherein seniors can be cited merely as an nonexclusive example. The hand grip element surprisingly leads to an improved upright body posture of the user or wearer and, due to the already described sensorimotor reflexive stimulation, to a positively vitalizing effect on the entire body of the handler, user or wearer.

The aforementioned persons hold a hand grip element in each case in the left and/or in the right hand when using the hand grip element according to the invention, wherein the hand grip elements with their shaped surfaces are designed in each case to be arranged on the left or right hand.

According to a further embodiment of the invention, the sixth shaped surface has a longitudinal extension which is substantially one-half the longitudinal extension of the hand grip body.

Because of this configuration, the index finger of the user or wearer of the hand grip element lies substantially against the sixth shaped surface over its entire longitudinal extension, wherein it is possible to adapt the hand grip element and the longitudinal extension of the sixth shaped surface to the size of the hand of the user or wearer by means of differently sized embodiments of the hand grip element with different overall lengths. The hand grip element can also be adapted and manufactured to be individualized to the size and shape of the respective hand or hands of the user.

According to a further embodiment of the invention, the hand grip body has a height extension running transversely to the longitudinal extension in a longitudinal sectional view, and the height extension increases from the first end region to approximately one-half the longitudinal extension and decreases from approximately one-half the longitudinal extension toward the second end region. Because of this configuration, the hand grip element has an initially increasing dimension in the direction of the height extension viewed in a sectional view from the side and, approximately in the region of one-half the longitudinal extension in the direction of the height, possesses the greatest dimension, and the height extension therefore decreases toward the second end region. Viewed from the side, the hand grip body therefore has a configuration similar to a mouse.

According to a further embodiment of the invention, the sixth shaped surface has a curvature that, proceeding in a longitudinal section from the first end region, decreases in the longitudinal direction of the hand grip body. The sixth shaped surface therefore has a relatively large curvature at the front end region of the hand grip body so that the index finger of the user follows this curvature, and the curvature of the sixth shaped surface therefore decreases, and the sixth shaped surface of the finger curvature correspondingly decreases toward the root of the finger, and a natural wearing comfort for the user or wearer of the hand grip element accordingly occurs.

According to a further embodiment of the invention it is also provided that the hand grip body, in a sectional view exhibiting its longitudinal axis, also possesses a longitudinal axial plane enclosing the longitudinal axis and running in the height extension of the hand grip body, proceeding from which the hand grip body has a specific first width extension toward the fourth shaped body, and the first width extension proceeding from the first end region toward the second end region initially increases up to the region adjacent to the fourth shaped surface and decreases in the region of the fourth shaped surface, and again increases from the fourth shaped surface toward the fifth shaped surface, and decreases again from the fifth shaped surface toward the second end region.

If the hand grip body is thus viewed from above, then its width extension initially increases from the first end region toward the fourth shaped surface after which the width extension then initially decreases in the region of the fourth shaped surface to form a recess or trough to accommodate the middle finger, and the width extension of the hand grip body then initially again increases from the fourth shaped surface toward the fifth shaped surface and then again decreases over the course of the fifth shaped surface toward the second end region.

It was already mentioned above that the hand grip body has the configuration similar to a mouse in a side view, and the just-described configuration of the hand grip body viewed from above also manifests the configuration similar to a mouse that leads to the establishment of considerable wearing comfort of the hand grip element according to the invention on the part of the user or wearer.

A further embodiment of the invention also provides that the hand grip body has a definite second width extension starting from the plane of the longitudinal axis toward the third shaped surface, and the second width extension starting from the first end region initially increases toward the second end region up to a region adjacent to the third shaped surface, and it decreases in the region of the third shaped surface up to the first shaped surface, and again increases along the first shaped surface toward the second end region.

Given the decreasing width of the hand grip body in the region of the third shaped surface toward the first shaped surface, a thumb recess is created to accommodate the thumb of the hand of the user or wearer. When the hand grip element is properly used, the thumb therefore lies in the thumb recess and abuts the third shaped surface, is guided thereby, and the tip of the thumb, or respectively the crest of the thumb, undergoes an alignment at the third shaped surface in a direction that is directed slightly upward.

It is also provided according to a further embodiment of the invention that the hand grip body possesses a top side having the second and/or sixth shaped surface and a bottom resting surface lying opposite the top side which possesses an outwardly curved configuration substantially along its entire longitudinal extension. This design of the hand grip body enables the middle finger, the ring finger and the little finger of the respective hand of the user or wearer to partially grasp around the hand grip body when arranged thereupon and lie against the bottom resting surface, and the wearing comfort of the hand grip element is thereby increased.

It is also provided according to a further embodiment of the invention that the hand grip body has an increasing curvature in the region of the second shaped surface starting from the transitional region of the sixth shaped surface to the second shaped surface toward the second end region which enables the hand grip body to fit against the palm and ball of the hand or respectively the thenar eminence, and a contact surface is created for tactile stimulation of the nerve cells lying in the region of the ball of the hand, or respectively thenar eminence of the hand of the wearer or user that triggers vegetative control pulses, which surprisingly assist with the assumption of an upright body posture by the user.

It is also provided according to a further embodiment of the invention that the hand grip body has a gap enclosing a region of the sixth shaped surface, and the gap, starting from a front region of the sixth shaped surface facing the first end region at which said sixth shaped surface is physically connected to the hand grip body, extends around the sixth shaped surface and holds it at a distance from the hand grip body. The sixth shaped surface is therefore physically connected to the hand grip body at its front region facing the first end region and is otherwise surrounded by a gap that holds the sixth shaped surface at a slight distance from the hand grip body.

In this case, the gap is designed to accommodate an elastic loop which can be releasably secured in the gap and is designed to accommodate the index finger. When using the hand grip element, the user or wearer of the hand grip element therefore inserts his index finger of the left or right hand into the elastic loop which is configured such that the index finger is held by the loop in a physical contact with the sixth shaped surface without however exerting excess contact pressure on the index finger such that the thus-achieved fixation of the index finger in position on the sixth shaped surface can also be maintained over several hours.

The fixation in position serves in this case to align the index finger in a direction to the front starting from the user or wearer of the hand grip element so that the index finger, or respectively index fingers of the user or wearer is/are always aligned in the direction of movement while walking or running, i.e., generally speaking during movement.

In this case, the loop can be made of an elastic material in the form of a washable, breathable fabric or material provided for medical and/or sports use which, for example, can also be provided with elastomer inlays, i.e., a material as for example used for compression stockings or thrombosis stockings. Releasably securing the elastic loop in the gap enables the loop to be easily removable from the gap and quickly washable with water and/or a cleanser when it becomes soiled or sweaty after the hand grip element is actively used by the user or wearer during sports activities.

It is also provided according to a further embodiment of the invention that in the transitional region between the first and the second shaped surface, an outwardly curved contact surface is formed that lies against the fold of the thenar eminence and the radial wrist starting in the transitional region from the first end region to the second end region when the hand grip element is arranged on the hand.

There are namely stimulation points under the skin at the transition region from the thumb to the wrist. These act on the radial artery and on the branches of the radial and medial nerves in the wrist. This contact causes a definite stimulation of the vegetative nervous system throughout the entire body of the user or wearer with positive consequences for the well-being and physical performance of the user or wearer so that the hand grip element can also contribute to the enhancement of the physical performance of the user.

It is also provided according to a further embodiment of the invention that the hand grip body is provided with an annular loop on the second end region which for example can also be designed elastically. To use the hand grip element, the user of the hand grip element guides his hand through the annular loop which encloses the wrist and fixes the relative position of the wrist to the hand grip element, and consequently the relative position of the contact surface to the fold of the thenar eminence and the radial wrist as well. Moreover, the annular loop also functions as a securing means against losing the hand grip element during active sports.

According to a further embodiment of the invention, it is also provided that the hand grip body is provided with an internally threaded sleeve in the region of the fifth shaped surface.

A pole as for example used in Nordic walking, or skiing, or cross-country skiing can be screwed into this internally threaded sleeve so that the hand grip element according to the invention can be used not just while running or walking, but also for example in the other cited sports.

It is also provided according to a further embodiment of the invention that the hand grip body has a closable receiving compartment that is accessible from the outside. For example, a mechanically and/or electrically actuated pulse generator can be inserted into this receiving compartment which, when moved, exerts a mechanical pulse on the sensory or tactile contact zones of the hand, or for example can exert an adjustable electrical pulse on the contact zones which can be interpreted by the human body as a target pulse for the heart rate which can for example cause the reduction of an elevated heart rate after active sports activity.

It is also provided according to a further embodiment of the invention that the hand grip body is designed in the form of two body halves which can be releasably secured to each other at a parting plane, and possesses a cavity in the interior for receiving the aforementioned pulse generator. The thus designed hand grip body can therefore be divided at the parting plane into two body halves or body parts so that the interior is accessible after separating the body halves or body parts to arrange or remove the pulse generator. The body halves or body parts can for example also be provided with latching means at the parting plane so that the body halves or body parts can be reproducibly latched to each other and therefore can be releasably connected to each other.

The bottommost of the two body halves could also be removed for proper use during running activities which would bring about a reduction of weight without changing the function or stability of the hand grip element.

The invention will be further explained below with reference to the drawing. In the drawing.

The figures shown in the subsequent drawing each show visible edges by continuously depicted lines of the three-dimensional hand grip element, and dashed lines for the sake of better visualization which are invisible in the shown perspective, however serve to better understand the hand grip element with a spatially complex design.

Figure 1:
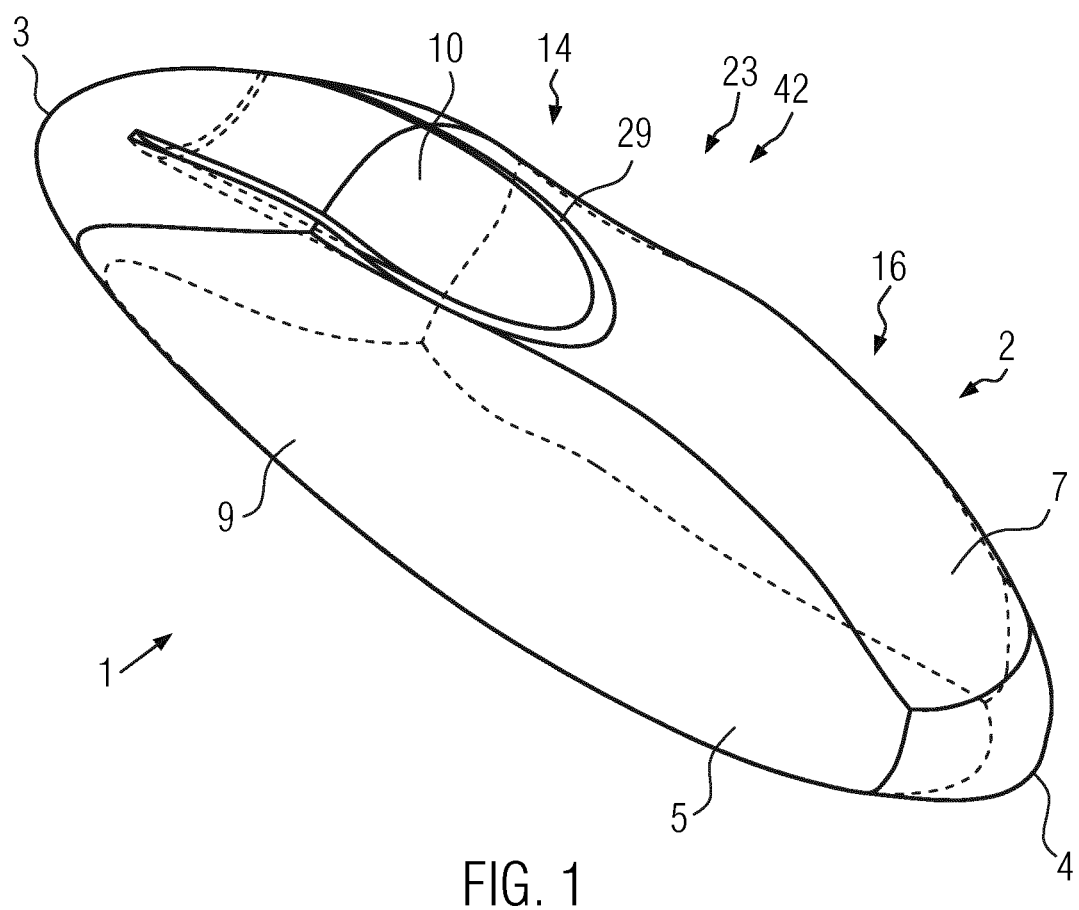
FIG. 1 shows a perspective view of the hand grip element for the right hand according to an embodiment pursuant to the present invention to illustrate some shaped surfaces.
Figure 3:
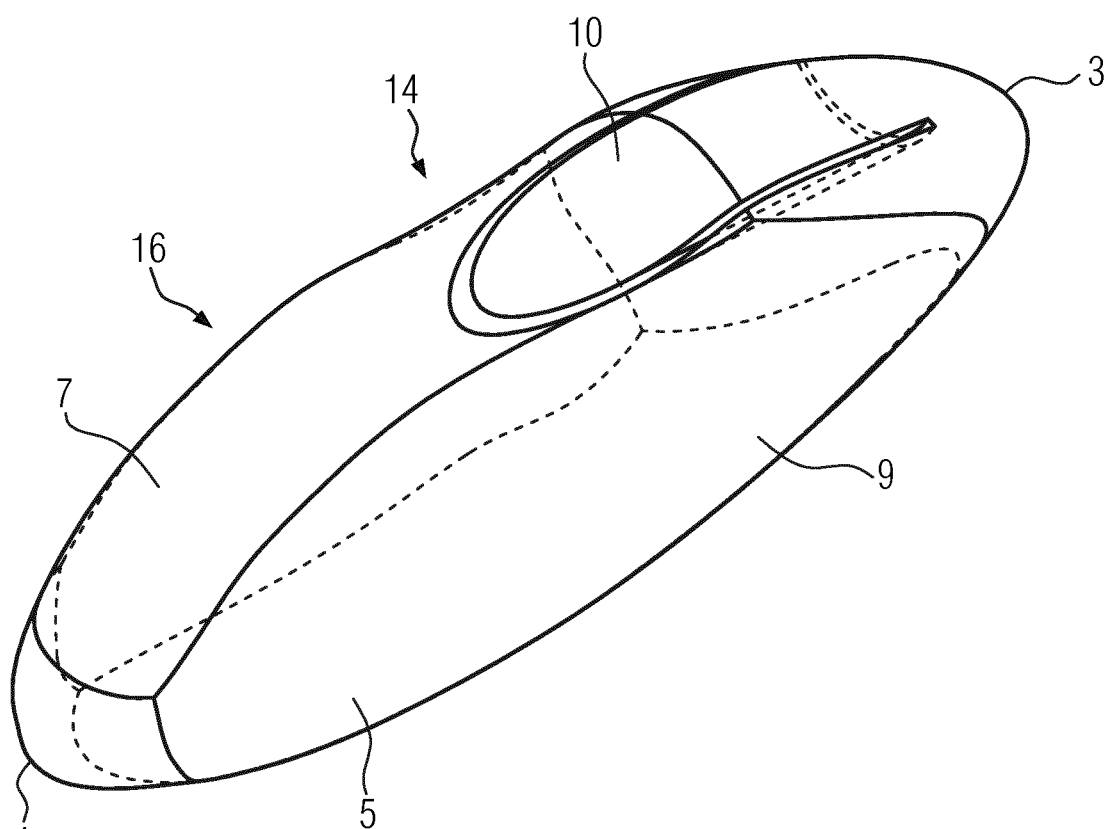
FIG. 3 shows a view similar to that in FIG. 1 which shows a hand grip element for the left hand.
Figure 4:
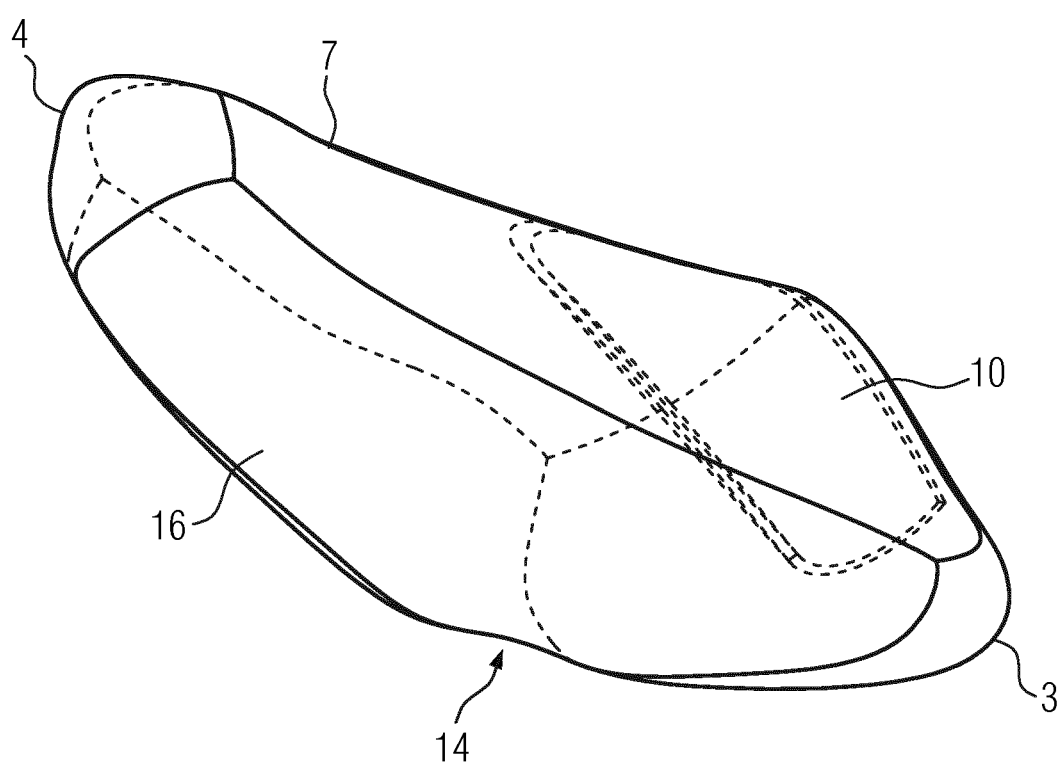
FIG. 4 shows a view similar to that in FIG. 2 which shows a hand grip element for the left hand.

FIG. 1 of the drawing shows a perspective view of an embodiment of a hand grip element 1 that is provided for the right hand of a user or wearer, or respectively user of the hand grip element 1 according to the invention. FIG. 3 of the drawing shows a similar view of a hand grip element for the left hand of the user.

The hand grip element 1 has an elongated hand grip body 2 which has a first or front end region 3 and a second or rear end region 4.

The hand grip body 2 possesses a plurality of shaped surfaces which are provided to arrange different regions or fingers of the human hand. At this point, reference is initially made to FIG. 14 of the drawing that shows a hand grip element 1 which is provided to be grasped by the right hand of the user and is shown arranged in the hand of the user.

Figure 15:
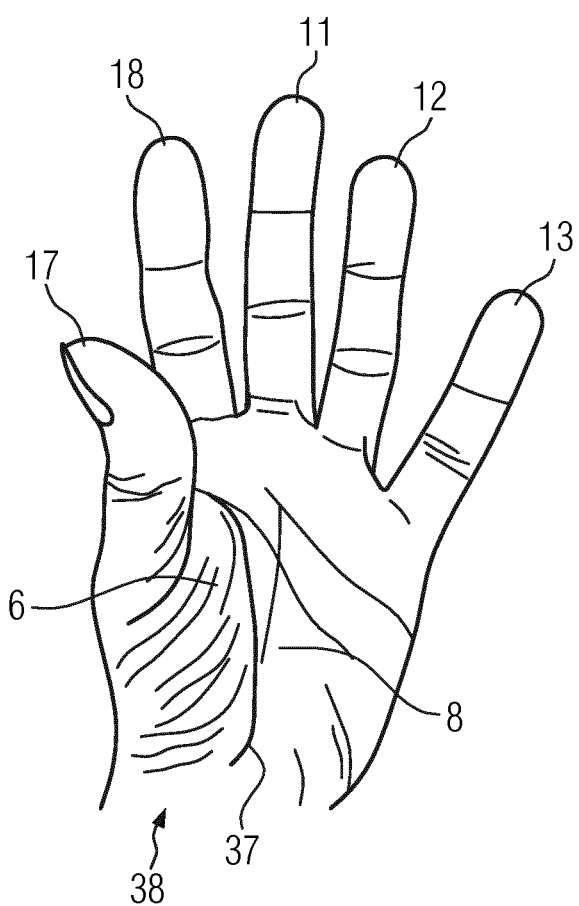
FIG. 15 shows the view of a left hand of the user or wearer to illustrate the fold of the thenar eminence.

A first shaped surface 5 is formed on the hand grip element 1 and is arranged adjacent to the second end region 4 for supporting a subregion of the ball of the hand or respectively the thenar eminence 6 of the human hand which is schematically shown in a schematic view in FIG. 15 of the drawing. The shaped surface 5 is designed curved outwardly as for example can be seen in the perspective view in FIG. 10 of the drawing.

Adjacent to the first shaped surface 5 is a second shaped surface 7 that is also designed curved outwardly and is designed to support a subregion of the palm 8—see FIG. 15—of the human hand.

Figure 14:
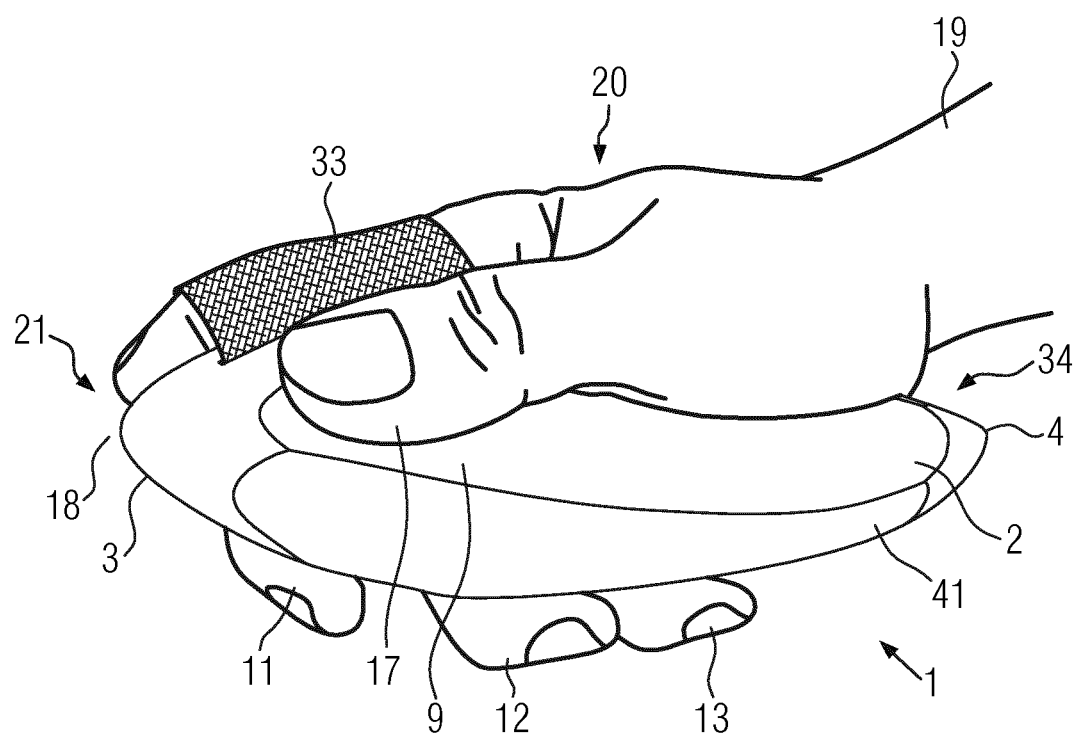
FIG. 14 shows a perspective view of a hand grip element as arranged in the right hand of a user or wearer.

Designed adjacent to the first shaped surface 1 is an inwardly curved third shaped surface 9 which is designed to support the substantially extended thumb 17 of the human hand, wherein this in turn can also be seen for example in FIG. 14 of the drawing.

On the top side of the hand grip body 2 shown in the plane of the drawing in FIG. 1 is a sixth shaped surface 10 which is designed to support the index finger 18 of the human hand, wherein this in turn can be best seen in FIG. 14 of the drawing.

If the user places the hand grip element 1 in his hand as shown in FIG. 14 of the drawing, the middle finger 11, the ring finger 12 and the little finger 13 of the hand are supported on other surfaces, or respectively shaped surfaces of the hand grip body 2 and therefore lie against the surfaces, or respectively shaped surfaces.

Figure 2:
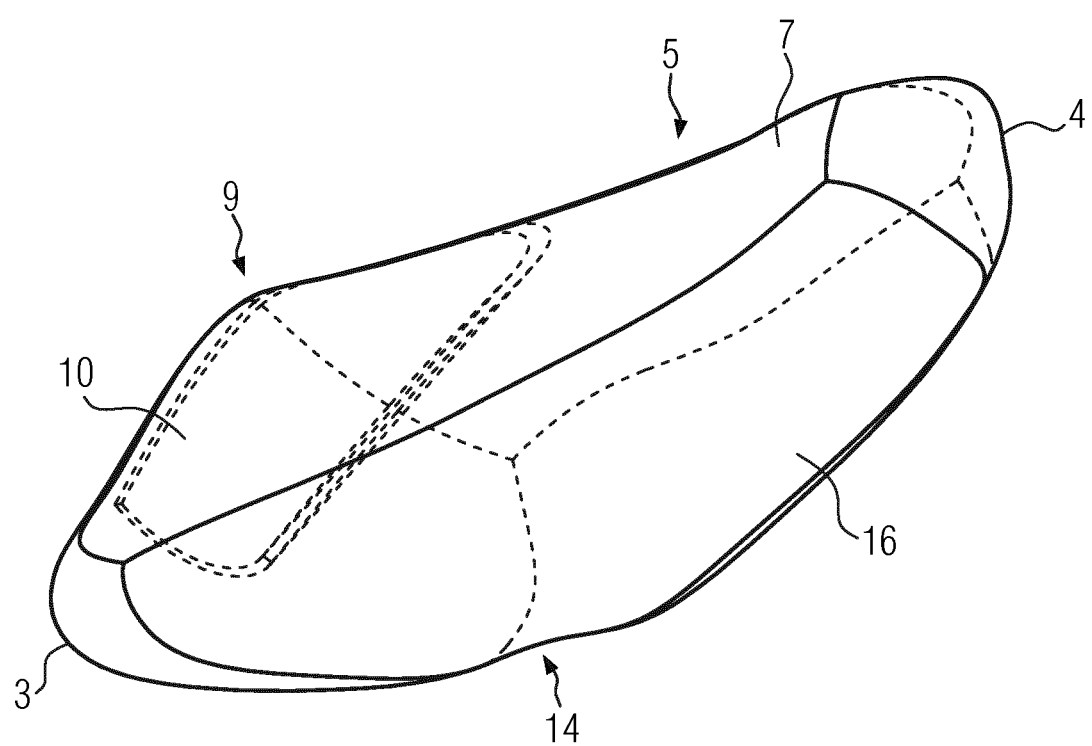
FIG. 2 shows another perspective view of the hand grip element for the right hand to illustrate other shaped surfaces.
Figure 6A:
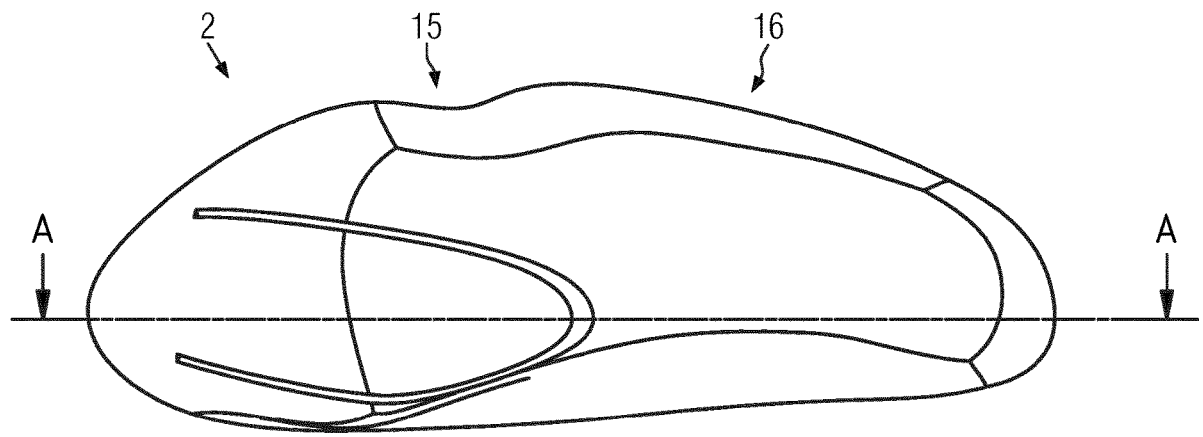
FIG. 6A shows the hand grip element in a view from above with a sectional course A-A.

Accordingly, the middle finger 11 contacts a fourth shaped surface 14 which is formed on the rear of the hand grip body 2 shown in the plane of the drawing in FIG. 1 and can be seen in greater detail in FIG. 2 of the drawing, and is designed in the shape of a recess or trough 15 and for example can also be seen in FIG. 6A.

Finally, the hand grip body 2 also has a fifth shaped surface 16 which is designed to support the ring finger 12 and for example can also be seen in FIG. 6A. The little finger 13 of the hand can also be supported against the fifth shaped surface 16.

FIG. 14 of the drawing shows that the hand grip body 2 with its shaped surfaces is designed such that the middle finger 11, the ring finger 12 and the little finger 13 at least partially grasp the hand grip body 2, whereas the third shaped surface 9 assigned to the thumb 17 is designed so that the thumb 17 assumes a substantially extended position oriented slightly upward on the third shaped surface 9, and the sixth shaped surface 10 is designed such that the index finger 18 when resting thereupon, assumes a position that is substantially directed forward and extended as can be seen in FIG. 14 of the drawing that shows the index finger 18 relative to the partially shown forearm 19 of the wearer or user or handler of the hand grip element 1.

The forearm 19 of the user assumes an angled position relative to the body of the user (not shown in greater detail) while walking or running that is oriented toward the front viewed from the body so that the index finger 18 arranged on the shaped surface 10 also assumes a position pointing away from the body and oriented toward the front during natural running or walking.

As already mentioned, FIG. 3 shows a hand grip element 1 in an embodiment for the left hand of the user so that a hand grip element for both the right and for the left hand is available to the user when using the hand grip element 1.

The hand grip element shown in FIG. 3 also has a first shaped surface 5 for supporting a subregion of the thenar eminence or ball of the hand 6 of the hand, and possesses a second shaped surface 7 for supporting a subregion of the palm 8. The thumb 17 of the left hand, in this case, of the user can be arranged on the third shaped surface 9 of the hand grip body 2 according to FIG. 3, and the middle finger 11 of the left hand of the user can be arranged on the fourth shaped surface 14 which is also formed in the shape of a trough or recess 15. The ring finger 12 and the little finger 13 of the left hand of the user again find a contact surface, or support surface, or respectively resting surface on the fifth shaped surface 16 of the hand grip body 2 according to FIG. 3.

As can be seen for example in FIGS. 1 and 3 of the drawing, the sixth shaped surface 10, viewed in the longitudinal direction of the hand grip body 2, extends substantially along half the longitudinal extension of the hand grip body 2 and thus provides a sufficiently long resting or support surface for the respective index finger 18 of the respective hand of the user.

Figure 6B:
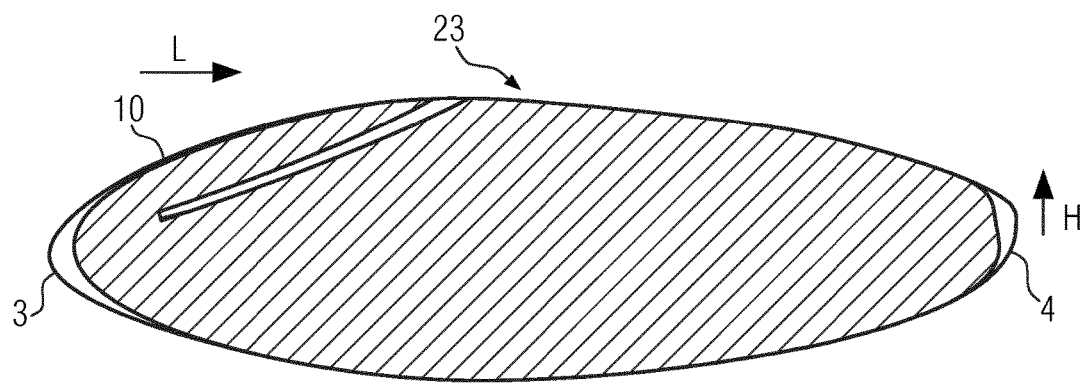
FIG. 6B shows the sectional view according to the sectional course A-A according to FIG. 6A.

FIG. 6A of the drawing shows a view of the hand grip body 2 with a line of intersection A-A to form a longitudinal sectional view that is shown in FIG. 6B of the drawing. The drawing serves to illustrate the height extension of the hand grip body 2, namely in a direction transverse to the longitudinal extension. As can readily be seen, the height extension measured in the direction of the arrow H initially increases from the first end region 3 in the direction of progression of the arrow L—which corresponds to the longitudinal direction of the hand grip element 1—namely into a region that approximately corresponds to half the longitudinal extension of the hand grip body 2, and then decreases again toward the second end region 4.

In this case, the sixth shaped surface 10 provided for arranging, or respectively receiving the index finger 18 of the user has a strong curvature in the region of the first end region 3, and the curvature of the sixth shaped surface gradually decreases toward the direction of the arrow L, i.e., from the first end region 3 toward the second end region 4, so that a sixth shaped surface 10 results at which the index finger 18 initially assumes a slight curvature corresponding to a natural position proceeding from the base 20 of the index finger up to the fingertip 21, and the curvature then gradually decreases toward the fingertip 21 of the index finger 18 so that the index finger 18 lies on the sixth shaped surface 10 corresponding overall to a natural finger posture, however when the hand grip element 1 is used by the user during natural walking or natural running, it assumes a position, or respectively posture facing away from the body pointed forward in the direction of movement.

Figure 5A:
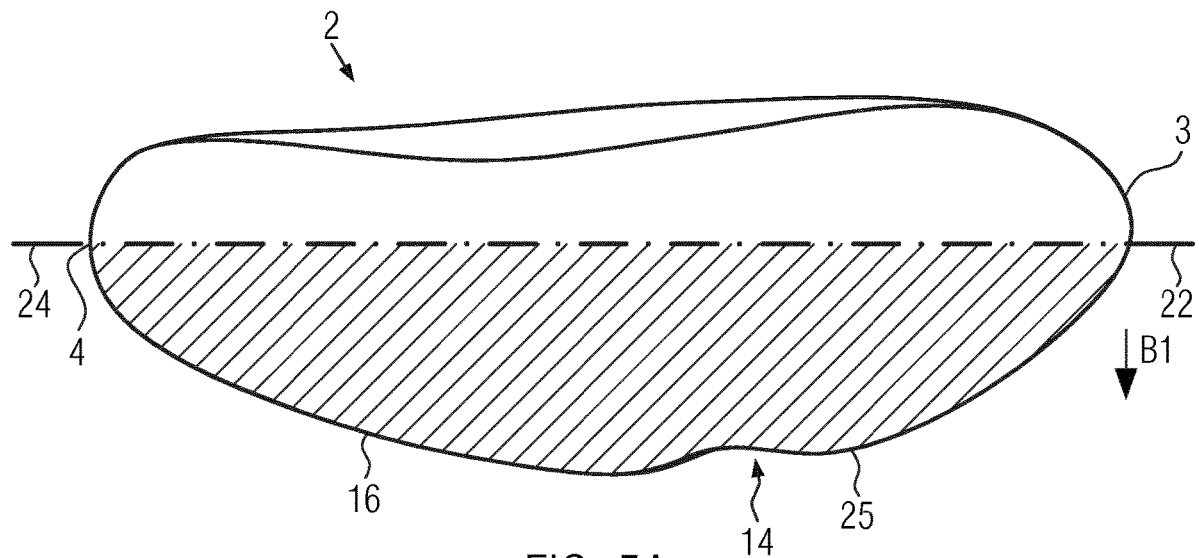
FIG. 5A shows the hand grip element in a partial sectional view to illustrate a first width extension B1.
Figure 5B:
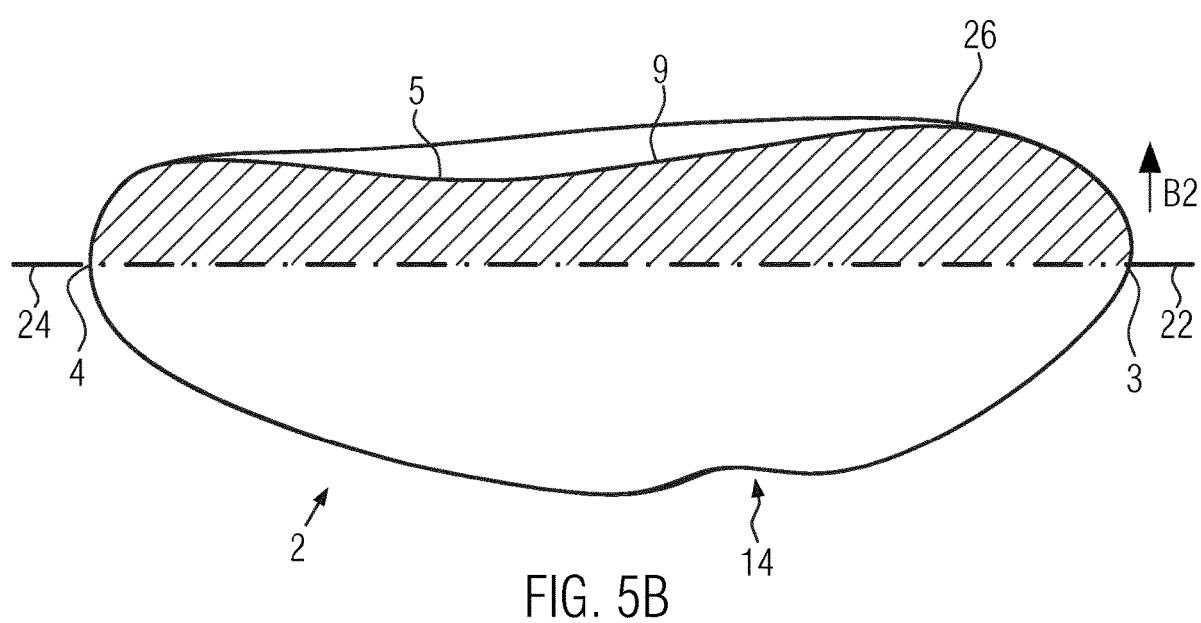
FIG. 5B shows the hand grip element in a partial sectional view to illustrate a second width extension B2.

FIG. 5A and FIG. 5B serve to illustrate the width extension of the hand grip body 2 of the hand grip element 1.

FIG. 5A shows a longitudinal axis 22 of the hand grip body 2 that spans a longitudinal axis plane 24 running in the direction of the height H according to FIG. 6B.

Viewed from the plane of the longitudinal axis 24, the hand grip body 2 has a first width extension B1 that initially increases from the first end region 3 toward the fourth shaped surface 14, namely up to a region 25 adjacent to the fourth shaped surface 14 in order to then decrease in the region of the fourth shaped surface 14, and to initially again increase in width from the fourth shaped surface 14 toward the fifth shaped surface 16 and then, over the contour of the fifth shaped surface 16, to again decrease in width starting from the fourth shaped surface 14 toward the second end region 4.

As can readily be seen in FIG. 5B, the hand grip body possesses a definite second width extension B2 viewed from the plane of the longitudinal axis 24 toward the third shaped surface 9, said width extension, starting from the first end region 3, initially increasing toward the second end region 4 up to a region 26 adjacent to the third shaped surface 9, and decreasing in width in the region of the third shaped surface 9 up to the first shaped surface 5, and the width then increasing again along the first shaped surface 5 toward the second end region 4.

Figure 7A:
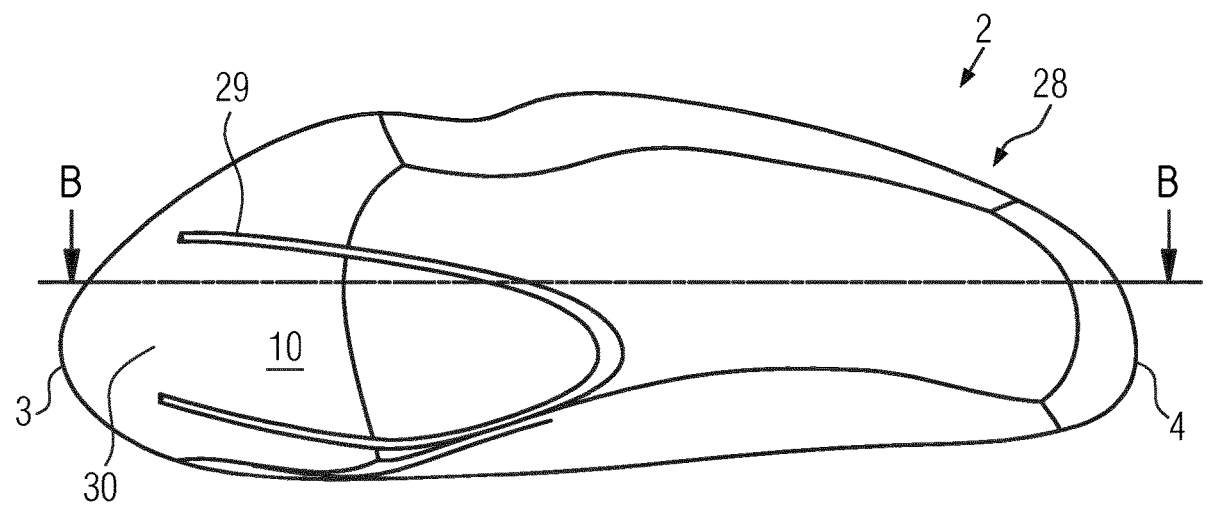
FIG. 7A shows the hand grip element in a view from above with a sectional course B-B.
Figure 7B:
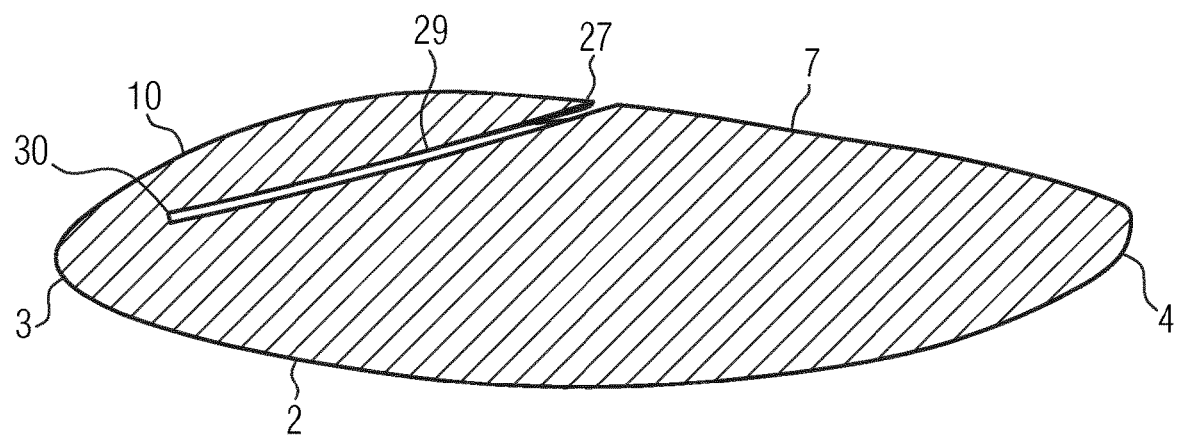
FIG. 7B shows the sectional view according to the sectional course B-B according to FIG. 7A.

FIG. 7A of the drawing again shows a plan view of the hand grip body 2 with a longitudinal sectional line B-B which yields a sectional view shown in FIG. 7B.

As can readily be seen, the hand grip body 2, starting from the transitional region 27 of the sixth shaped surface 10 to the second shaped surface 7, possesses a gradually increasing curvature toward the second end region 4 so that a fitting surface results which gently receives the palm 8.

As can for example be seen in FIG. 7A, the hand grip body 2 has a gap 29 enclosing a region of the sixth shaped surface 10, wherein the gap 29, starting from a front region 30 of the sixth shaped surface 10 facing the first end region 3 at which said sixth shaped surface is physically connected to the hand grip body 2, extends around the sixth shaped surface 10 and holds it at a distance from the hand grip body 2.

Whereas the course of the gap 29 visible to the outside is shown in FIG. 7A, FIG. 7B shows the gap 29 entering the hand grip body 2 which runs to the front region 30 at which the sixth shaped surface 10 is physically connected to the hand grip body 2.

Figure 8:
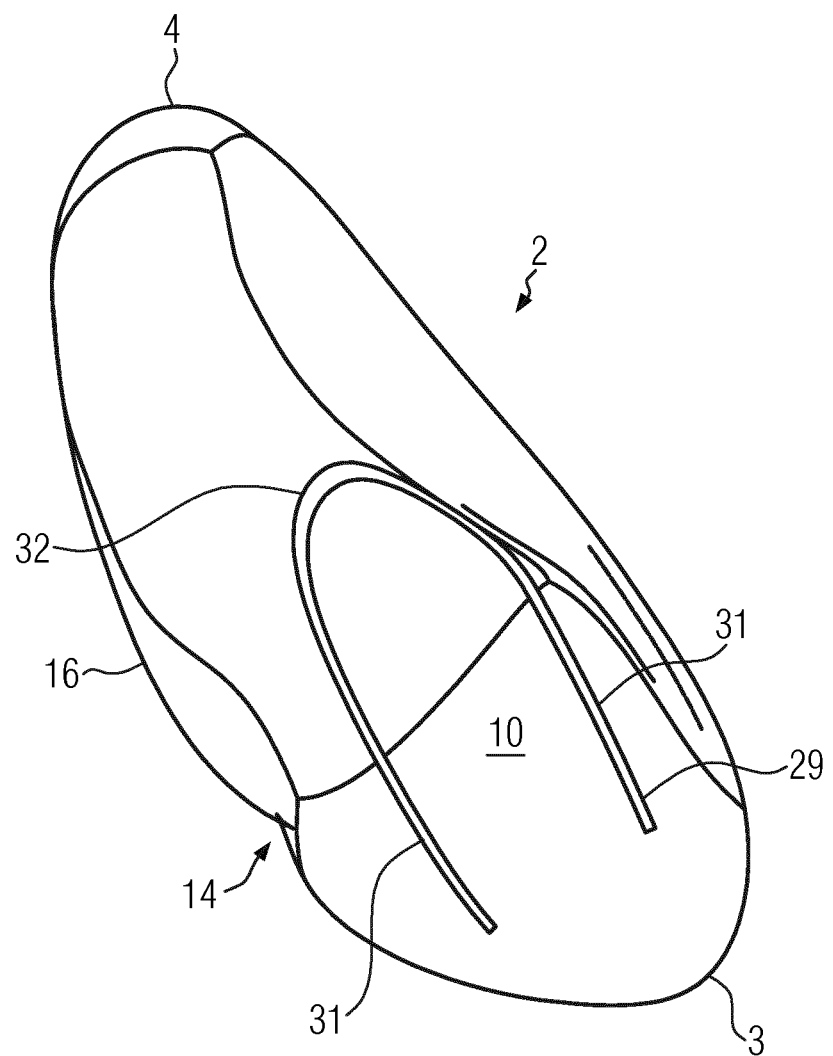
FIG. 8 shows a perspective view of the hand grip element for illustrating a gap substantially surrounding the sixth shaped surface.

FIG. 8 shows the gap 29 in a bird's eye view of the hand grip body 2 which reveals that the gap 29 has a U-shaped configuration in a plan view and encloses the sixth shaped surface 10 in the region of both legs 31, as well as the base 32 of the U-shaped configuration connecting the two legs 31.

Figure 13:
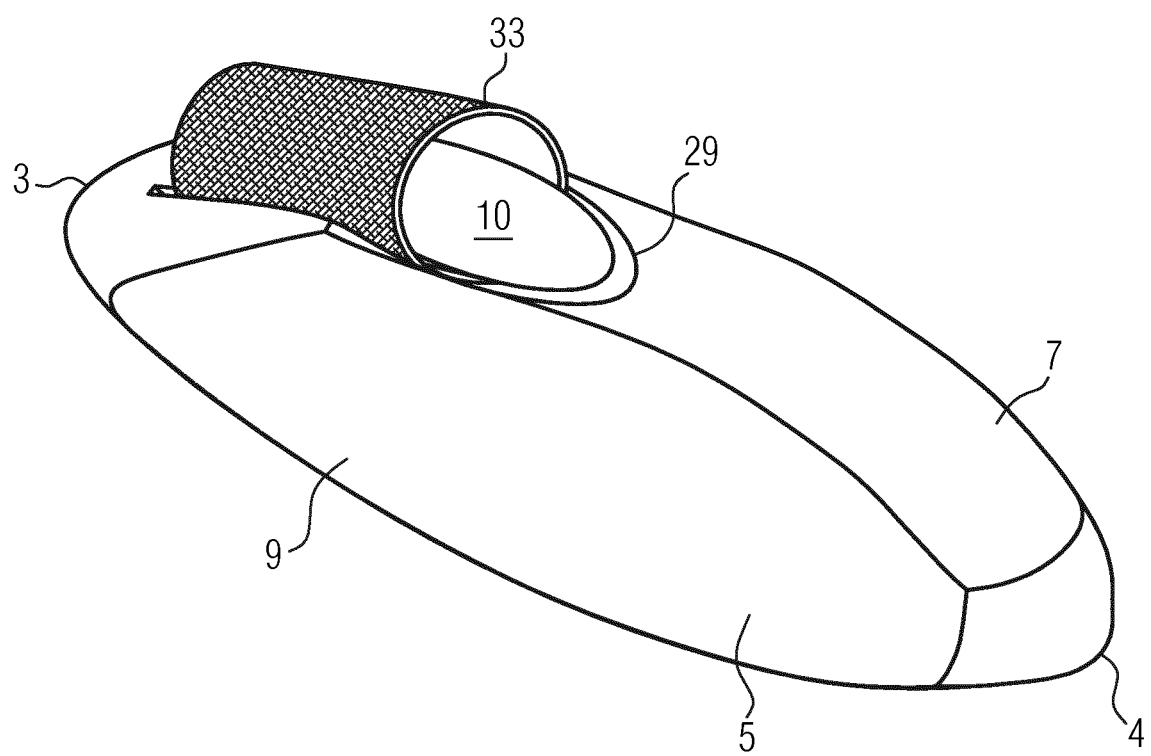
FIG. 13 shows a perspective view of the hand grip element with a finger loop.

The function of the gap 29 is apparent in FIG. 13 of the drawing. An elastic loop 33 can be releasably introduced into the gap 29 such that the tubular annular loop 33 shaped from an elastic material can be introduced into the gap and undergoes clamping in the region of the front section 30, and is thereby secured in the gap 29. The material forming the annular loop 33 can for example be formed similar to the material to form a compression stocking and encloses the index finger 18 of the hand of the user when the hand grip element 1 is properly used such that a subregion of the longitudinal extension of the index finger is enclosed by the elastically stretched annular loop 33, and the index finger 18 thus undergoes a fixation in position, or respectively positioning on the sixth shaped surface 10 and is aligned in a forward direction, i.e., in the direction of movement viewed from the body of the user or handler of the hand grip element 1.

Figure 9:
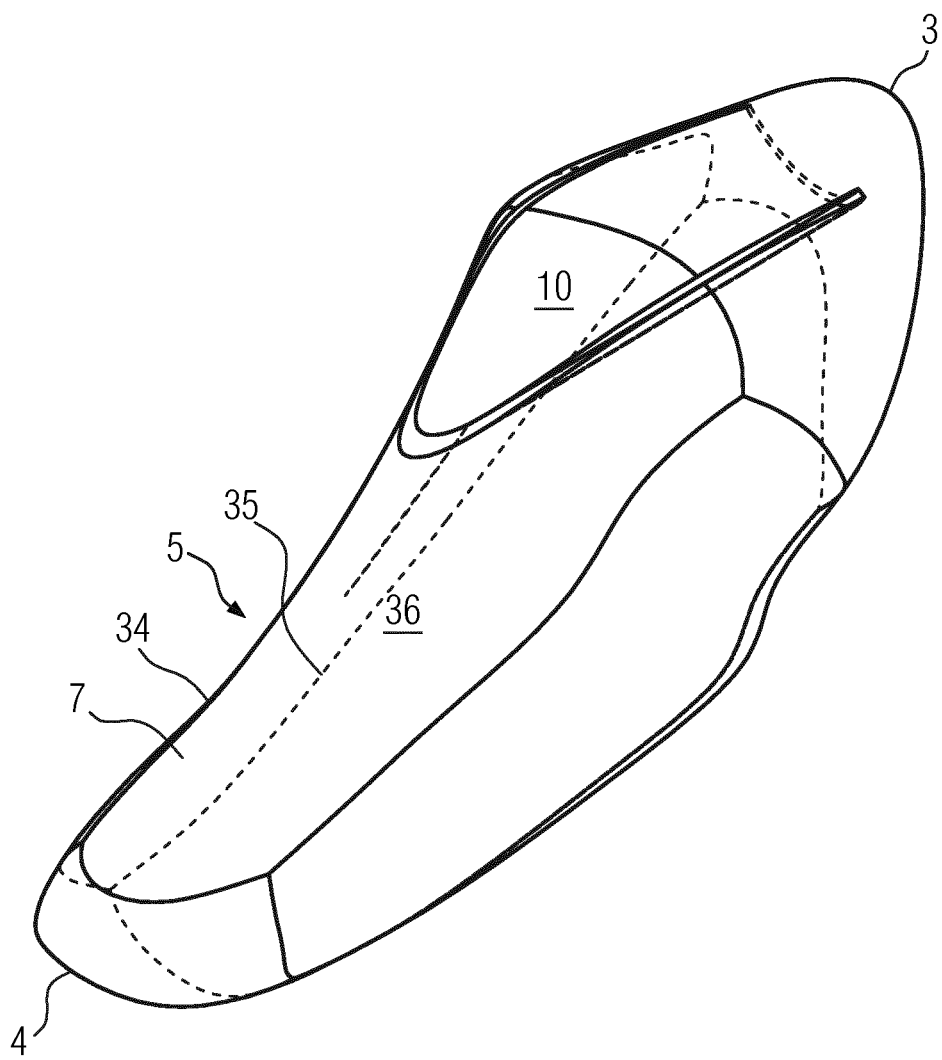
FIG. 9 shows a perspective view of the hand grip element for illustrating a contact surface between the first and the second shaped surface.

FIG. 9 of the drawing shows a perspective view of the hand grip element 1 with the second shaped surface 7 and the first shaped surface 5, which is only partially visible due to the chosen perspective, and the contact surface 34 formed between the first shaped surface 5 and the second shaped surface 7 that, as is shown by the visible edge 35, is designed curved outwardly starting from the inner compartment 36 of the hand grip body 2.

As can be seen in the perspective view in FIG. 14, the contact surface 34 lies on the fold of the thenar eminence 37 (FIG. 15) and on the radial wrist 38 starting in the transitional region from the first end region 3 to the second end region 4 when the hand grip element 1 is used properly.

Figure 10:
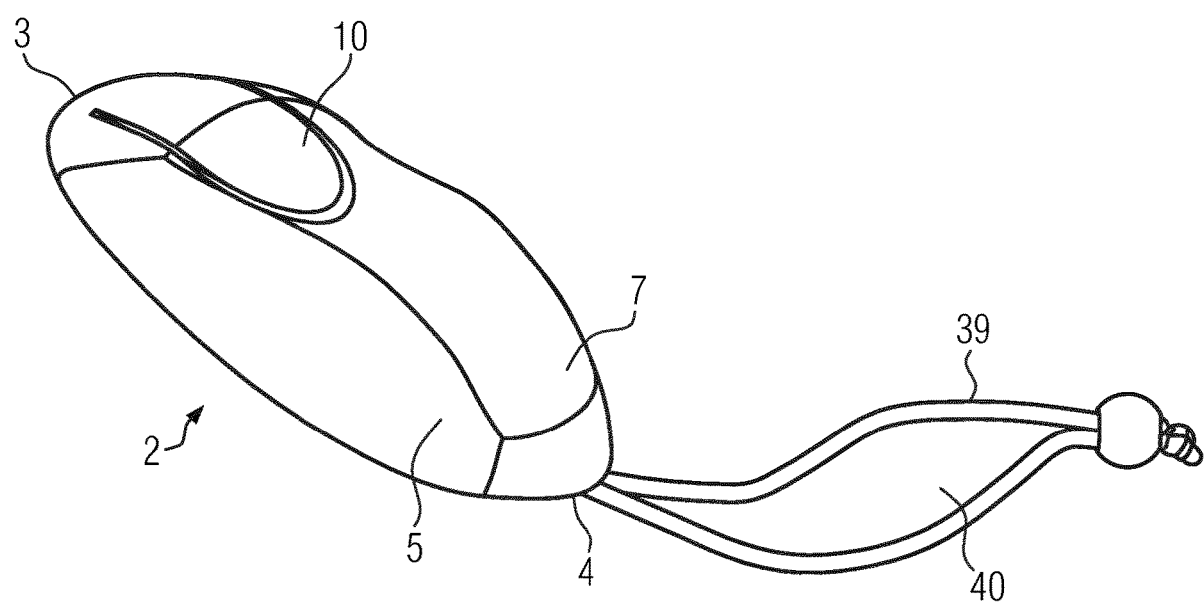
FIG. 10 shows a perspective view of the hand grip element with an annular loop.

FIG. 10 of the drawing shows the hand grip body 2 with an annular loop 39 that is provided in the region of the rear or second end region 4, and through the opening 40 of which the user of the hand grip element 1 according to the invention inserts his hand and then grasps the hand grip body 2 as can be seen in FIG. 14 of the drawing. In so doing, the annular loop 39 serves on the one hand as an aid against unintentionally losing the hand grip element 1 during a sports activity, and also as an aid to assist with the maintenance of the position of the fold of the thenar eminence 37 and the radial wrist 38 relative to the contact surface 34. The annular loop 39 can be made of an elastic or semi-elastic strip of varying width or thickness and with a round or also rectangular cross-section.

The design of the hand grip element 1 with the contact surface 34 and its contact with the sensors, nerve cells and nerve fibers in the region of the fold of the thenar eminence 37 and the thenar eminence 6 and the radial artery in the wrist lying directly under the skin instigates contact stimulation and therefore activation of the entire circulatory system of the user of the hand grip element 1 according to the invention.

As can be seen for example in FIG. 1 of the drawing, the second shaped surface 7 and the sixth shaped surface 10 form a top side 42 of the hand grip body 2, and the hand grip body 2 has a resting surface 41 that is opposite the top side 42 and, as shown in FIG. 14 of the drawing, has an outwardly curved configuration substantially along its entire longitudinal extension. A gently curved abutment surface for the arrangement of the respective fingertips of the middle finger, the ring finger and the little finger is achieved by means of this outwardly curved configuration, as can also be seen in FIG. 14 of the drawing.

Figure 11:
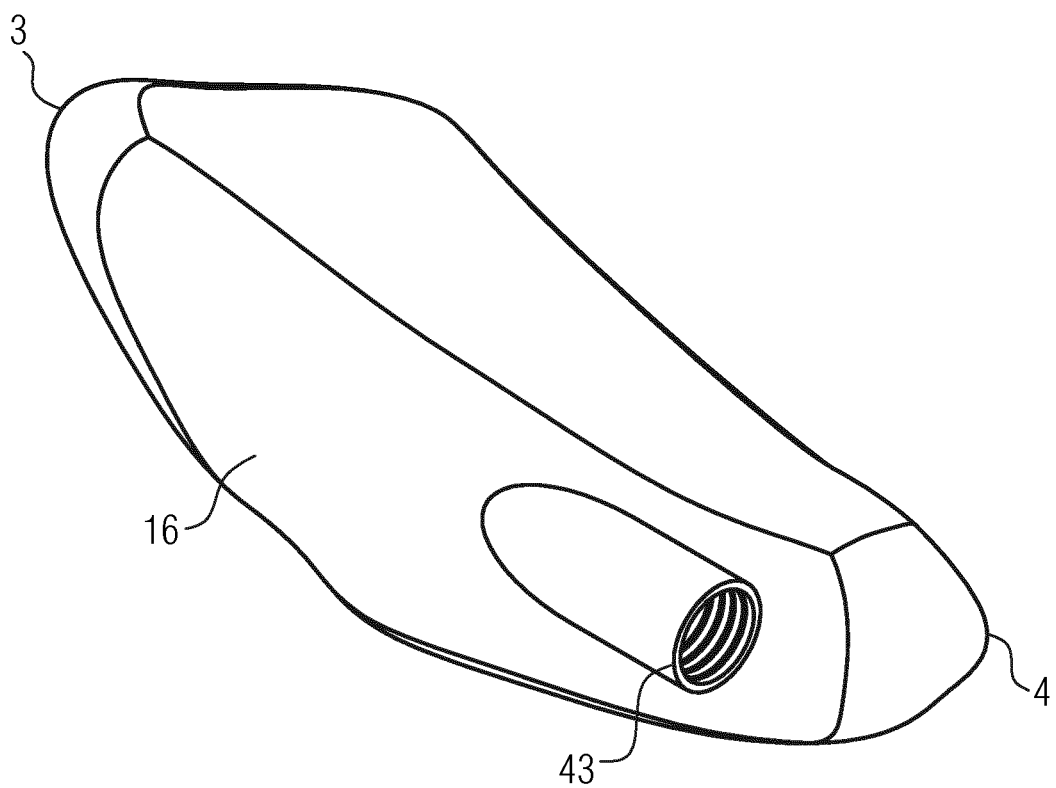
FIG. 11 shows a perspective view of the hand grip element in a view from below to illustrate an internally threaded sleeve provided in a shaped surface.

FIG. 11 of the drawing shows an internally threaded sleeve 43 arranged in the region of the fifth shaped surface 16 into which for example a pole (not shown in greater detail) as for example used in Nordic walking, or skiing, or cross-country skiing is screwed so that the hand grip element according to the invention can be used not just while running or walking, but also for example in the other cited types of sports.

By designing the hand grip element 1 with the internally threaded sleeve 43, the hand grip element according to the invention can be used both during normal walking or running as well as a main body for accommodating a pole as described above. This option advantageously expands the range of use of the hand grip element according to the invention.

Figure 12:
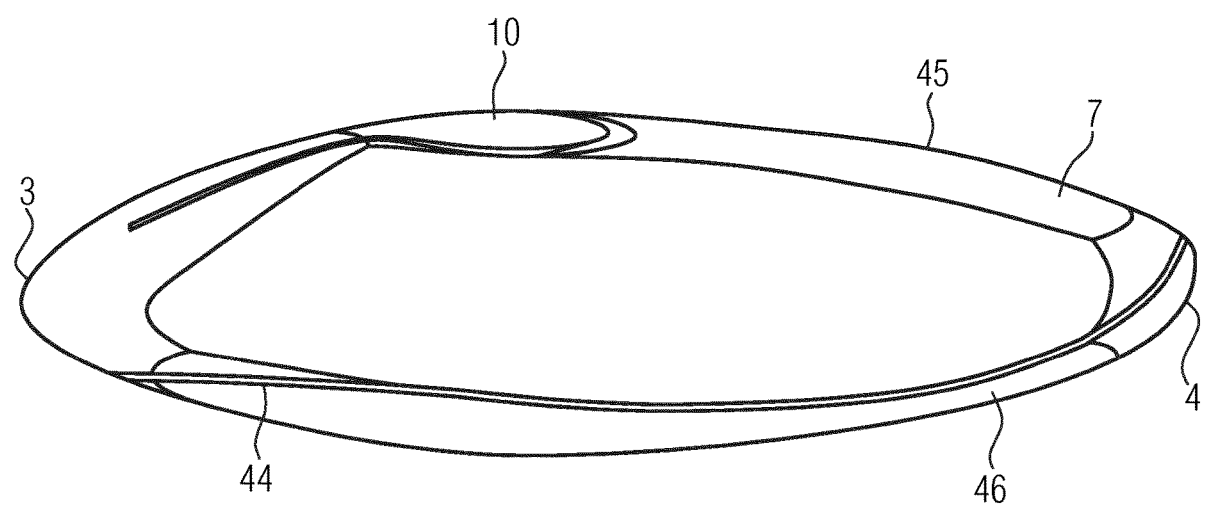
FIG. 12 shows a perspective view of the hand grip element with a hand grip body with two body halves.

FIG. 12 of the drawing shows another embodiment of the hand grip element 1 according to the invention with a hand grip body 2 that has a parting plane 44 which divides the hand grip body 2 into two body halves, i.e., a first partial body 45 and a second partial body 46.

Figure 16:
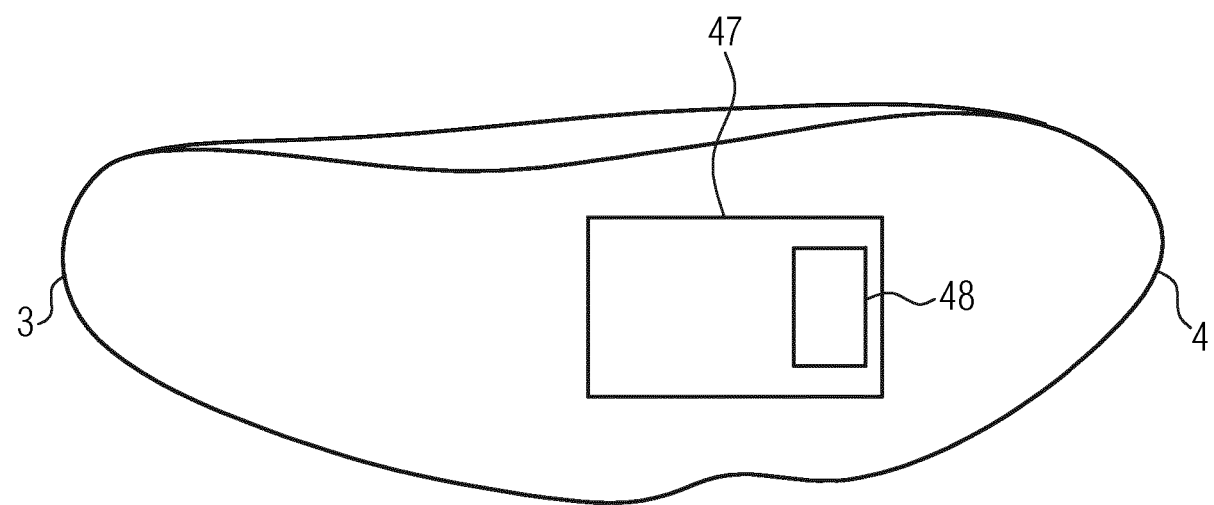
FIG. 16 shows a view of a body half of a divided hand grip element with an inner compartment.

The advantage of this embodiment is that a closable receiving compartment or inner compartment 47 arises in the interior of a partial body, or both partial bodies, by releasably securing the two partial bodies 45, 46 to each other at the parting plane 44 as schematically shown in FIG. 16 of the drawing. This receiving compartment or inner compartment 47 serves to receive a mechanically and/or electrically actuated pulse generator, or a pulse generator apparatus 48.

This optionally available pulse generator apparatus can exert a mechanical or for example adjustable electrical pulse as well to the tactile contact zones of the hand in the movement of the user with the hand grip element according to the invention which can be interpreted by the human body as a target pulse for the heart rate, which for example can cause reduction of an elevated heart rate after active sports activity.

As readily revealed in the figures, the overall hand grip element according to the invention possesses an elongated configuration and resembles an elongated body of a mouse in terms of visual appearance. When using the hand grip element according to the invention, a user can hold a hand grip element both in the left hand as well as in the right hand, and thereby achieves a position of the respective index finger in a direction oriented to the front in the direction of movement while walking or running, and also a position of the thumb lying against the respective hand grip element in the direction of movement and oriented slightly upward.

This posture produces a physiological benefit to the user which is medically founded in that it has been shown that the hand posture achieved with the hand grip element according to the invention leads to an upright body posture, and a reflexive stimulation of the body of the user also occurs, which is specifically supported by the contact between the above-described contact surface of the hand grip element with the thenar eminence and the radial wrist of the user.

The hand grip element, or respectively the hand grip body can be made from different materials; care should be taken for the choice of material to yield a pleasant feel for the user, and it is also advantageous when the material conducts heat well and is hypoallergenic. Advantageously, a plastic material can be used; however, an embodiment for example consisting of a wood material is also possible.

The surface design can be oriented in a nuanced manner around the needs of the user, modern materials as well as new production methods since the touch plays an important role in optimum utility.

The hand grip element yields an optimized, natural body posture and hand posture for the user, and internally stabilizes the physical state of equilibrium and the bodily stresses accumulated by the body. It has been shown that the tactile stimulus caused by the hand grip element at the areas of the skin at the thenar eminence and at the wrist instigates a reflexive sensorimotor stimulation which has a positively vitalizing effect on the entire body of the user.

The hand grip element according to the invention has an especially positive effect when the user is walking and running with the hand grip element, i.e., in all types of fast forward movement, and also in all types of running sports. The faster the movement of the user, the greater the importance of a posture of the index finger and thumb specifically oriented in the direction of movement for the physiological well-being and physical performance of the user. The hand grip element according to the invention surprisingly supports the quasi-automated assumption of an upright body posture by the user and can therefore bring about a positive effect to users with a basically somewhat bent body posture to straighten the body to achieve a natural and upright body posture.

The human hand possesses a very high number of sensors, nerve cells and nerve fibers that are addressed by the hand grip element according to the invention to achieve stimuli by touch. The hand grip element lies against the wrist in the region of the radial artery lying just under the skin and exerts contact stimulus thereupon by touch which causes an activation of the circulatory system of the user. At the transition from the thumb to the wrist, there are stimulation points under the skin that act on the radial artery and the nerve branches of the radial and medial nerves in the medial wrist. From the specific tactile touch of these hand areas, the hand grip element according to the invention causes a definite stimulation of the vegetative nervous system with consequences for the user's well-being and performance that are experienced as pleasant by the user.

With respect to the features of the invention that are not further explained in detail, reference is moreover expressly made to the claims and drawing.

LIST OF REFERENCE SIGNS

1. Hand grip element
2. Hand grip body
3. End region
4. Second end region
5. First shaped surface
6. Thenar eminence, ball of the hand
7. Second shaped surface
8. Palm
9. Third shaped surface
10. Sixth shaped surface
11. Middle finger
12. Ring finger
13. Little finger
14. Fourth shaped surface
15. Recess, trough
16. Fifth shaped surface
17. Thumb
18. Index finger
19. Forearm
20. Base
21. Fingertip
22. Longitudinal axis
23. Subregion
24. Longitudinal axis plane
25. Region
26. Region
27. Transitional region
28. Fitting surface
29. Gap
30. Front region
31. Leg
32. Base
33. Elastic loop
34. Contact surface
35. Visible edges
36. Inner compartment
37. Fold of the thenar eminence
38. Radial wrist
39. Annular loop
40. Opening
41. Resting surface
42. Top side
43. Internally threaded sleeve
44. Parting plane
45. First partial body
46. Second partial body
47. Receiving compartment
48. Pulse generator apparatus
H: Height
L: Longitudinal direction
B1: First width extension
B2: Second width extension

The invention claimed is:
1. A hand grip element comprising an elongated hand grip body having a first end region and a second end region arranged at a distance from the first end region in a longi- tudinal direction extending along the elongated hand grip body from the first end region to the second end region,
  wherein the hand grip body includes:
    a top side between the first end region and the second end region, and a first side opposite a second side between the first end region and the second end region,
    a first shaped surface located adjacent to the second end region on the first side and having a curved subregion surface to support a subregion of the ball of the human hand,
    second shaped surface on the top side located adjacent to the first shaped surface to support a subregion of the palm, the second shaped surface being outwardly curved or convex relative to an interior of the hand grip body,
    third shaped surface adjacent to the first shaped surface on the first side to support the substantially extended thumb, the third shaped surface being inwardly curved or concave relative to the interior,
    fourth shaped surface lying substantially opposite the third shaped surface on the second side to support the middle finger, the fourth shaped surface being outwardly curved,
    a fifth shaped surface adjacent to the fourth shaped surface on the second side to support the ring finger, the fifth shaped surface being outwardly curved, and
    a sixth shaped surface on the top side to support the index finger in a substantially stretched out position, wherein the sixth shaped surface, starting from a subregion of the second shaped surface spaced apart from the second end region of the hand grip body, extends toward the first end region and runs substantially in the longitudinal direction of the hand grip body, the sixth shaped surface being located between the third shaped surface and the fourth shaped surface.

2. The hand grip element according to claim 1, wherein the sixth shaped surface has a longitudinal extension which is substantially one-half the longitudinal extension of the hand grip body.

3. The hand grip element according to claim 1, wherein the hand grip body has an end surface having a height running transversely to the longitudinal direction in a longitudinal sectional view of the hand grip body, and the end surface increases from the first end region to approximately one-half the height and decreases from approximately one-half the height toward the second end region.

4. The hand grip element according to claim 1, wherein the sixth shaped surface has a curvature relative to a longitudinal axis of the hand grip body, which, proceeding in a longitudinal sectional view from the first end region, decreases in the longitudinal direction of the hand grip body.

5. The hand grip element according to claim 3, wherein the hand grip body, in a sectional view of the hand grip body exhibiting a longitudinal axis extending between the first end region and the second end region, possesses a plane defined by the longitudinal axis and the height of the hand grip body, proceeding from which the hand grip body has a specific first width extension toward the fourth shaped surface, and the first width extension proceeding from the first end region toward the second end region initially increases up to the region adjacent to the fourth shaped surface and decreases in the region of the fourth shaped surface, and again increases from the fourth shaped surface toward the fifth shaped surface, and decreases again from the fifth shaped surface toward the second end region.

6. The hand grip element according to claim 5, wherein the hand grip body has a definite second width extension starting from the plane of the longitudinal axis toward the third shaped surface, and the second width extension starting from the first end region initially increases toward the second end region up to a region adjacent to the third shaped surface, and it decreases in the region of the third shaped surface up to the first shaped surface, and again increases along the first shaped surface toward the second end region.

7. The hand grip element according to claim 1, wherein the hand grip body possesses a bottom resting surface lying opposite the top side, the bottom resting surface being outwardly curved relative to the interior substantially along its entire longitudinal extension of the bottom resting surface.

8. The hand grip element according to claim 1, wherein the hand grip body has an increasing curvature relative to a longitudinal axis of the hand grip body in the region of the second shaped surface starting from the transitional region of the sixth shaped surface to the second shaped surface toward the second end region.

9. The hand grip element according to claim 1, wherein the hand grip body has a gap enclosing a region of the sixth shaped surface, and the gap, starting from a front region of the sixth shaped surface facing the first end region at which said sixth shaped surface is physically connected to the hand grip body, extends around the sixth shaped surface and holds it at a distance from the hand grip body.

10. The hand grip element according to claim 9, wherein the gap is designed to accommodate an elastic loop which can be releasably secured in the gap and is designed to accommodate the index finger.

11. The hand grip element according to claim 1, wherein in the transitional region between the first and the second shaped surface, an outwardly curved contact surface is formed that lies against the fold of the thenar eminence and the radial wrist starting in the transitional region from the first end region to the second end region when the hand grip element is arranged on the hand.

12. The hand grip element according to claim 1, wherein the hand grip body is provided with an annular loop on the second end region.

13. The hand grip element according to claim 7, wherein the hand grip body is provided with an internally threaded sleeve in the region of the fifth shaped surface.

14. The hand grip element according to claim 1, wherein the hand grip body has a closable receiving compartment that is accessible from the outside.

15. The hand grip element according to claim 1, wherein the hand grip body is designed in the form of two body halves which can be releasably secured to each other at a parting plane.

16. The hand grip element according to claim 1, wherein the first shaped surface is curved inwardly relative to the interior.

17. The hand grip element according to claim 1, wherein the hand grip body is provided with at least one mechanically and/or electrically actuated pulse generator apparatus.

18. A hand grip element having an elongated hand grip body with a first end region and, arranged at a distance thereto in a longitudinal direction, a second end region, the longitudinal direction extending along the elongated hand grip body from the first end region to the second end region,
  wherein the hand grip body has a first shaped surface located adjacent to the second end region, with a curved subregion for supporting a subregion of the ball of the human hand, and an outwardly curved second shaped surface located adjacent to the first shaped surface for supporting a subregion of the palm, and an inwardly curved third shaped surface adjacent to the first shaped surface for supporting the substantially extended thumb, and an outwardly curved fourth shaped surface lying substantially opposite the third shaped surface for supporting the middle finger, adjacent to which fourth shaped surface an outwardly curved fifth shaped surface is provided for supporting the ring finger, and the hand grip body has a sixth shaped surface provided to support the index finger in a substantially stretched out position, wherein the sixth shaped surface, starting from a subregion of the second shaped surface spaced apart from the second end region of the hand grip body, extends toward the first end region and runs substantially in the longitudinal direction of the hand grip body, and wherein the hand grip body has a height running transversely to the longitudinal direction, and the height increases from the first end region to approximately one-half the height and decreases from approximately one-half the height toward the second end region.

* * * * *